US008080559B2

(12) United States Patent
Akella et al.

(10) Patent No.: US 8,080,559 B2
(45) Date of Patent: *Dec. 20, 2011

(54) 5(S)-(2'-HYDROXYETHOXY)-20(S)-CAMPTO-THECIN AND ITS PREPARATION AND USE FOR THE TREATMENT OF CANCER

(75) Inventors: Venkateswarlu Akella, Hyderabad (IN);
Shanavas Alikunju, Secunderabad (IN);
Ajaya Kumar Reka, Hyderabad (IN);
Ramesh Mullangi, Hyderabad (IN);
Raju Sirisilla, Hyderabad (IN);
Subrahmanyam Duvvuri, Hyderabad (IN); Sriram Rajagopal, Chennai (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/577,399

(22) Filed: Oct. 12, 2009

(65) Prior Publication Data

US 2010/0063083 A1 Mar. 11, 2010

Related U.S. Application Data

(62) Division of application No. 11/753,432, filed on May 24, 2007, now Pat. No. 7,601,733.

(60) Provisional application No. 60/887,416, filed on Jan. 31, 2007.

(30) Foreign Application Priority Data

May 24, 2006 (IN) .............................. 897/CHE/2006

(51) Int. Cl.
*A61K 31/4745* (2006.01)
*C07D 491/22* (2006.01)
(52) U.S. Cl. .......................................... 514/283; 546/48
(58) Field of Classification Search .................. 514/283; 546/48
See application file for complete search history.

(56) References Cited

U.S. PATENT DOCUMENTS 6,177,439 B1   1/2001  Duvvuri et al.
7,601,732 B2 * 10/2009  Akella et al. .................. 514/283
7,601,733 B2 * 10/2009  Akella et al. .................. 514/283

OTHER PUBLICATIONS

Benet et al., Appendix II Design and Optimization of Dosage Regimens; Pharmacokinetic Data, Goodman & Goodman's The Pharmacological Basis of Therapeutics, Ninth Edition, pp. 1707-1711 (1996).
Wall et al., Plant Antitumor Agents. I. The Isolation and Structure of Camptothecin, a Novel Alkaloidal Leukemia and Tumor Inhibitor from Camptotheca acuminata, Journal of the American Chemical Society, (1996), pp. 3888-3890, Volune-Issue 88:16, ACS Publications, Washington, DC.
Poynter et al., Coulometric Karl Fischer titration simplifies water content testing, Oil & Gas Journal, (1994), pp. 1-5, vol.-Issue 92:15, Kam Controls Inc., Houston, TX.
Monks, et al., Feasibility of a High-Flux Anticancer Drug Screen Using a Diverse Panel of Cultured Human Tumor Cell Lines, Journal of the National Cancer Institute, (Jun. 5, 1991), pp. 757-766, Volune-Issue 83:11.
Stewart et al., Gefitinib Enhances the Antitumor Activity and Oral Bioavailability of Irinotecan in Mice, Cancer Research, Oct. 15, 2004), pp. 7491-7499, Volune-Issue 64:2.
Gorlick et al., Biology of Childhood Osteogenic Sarcoma and Potential Targets for Therapeutic Development: Meeting Summary, Clinical Cancer Research, (Nov. 15, 2003), pp. 5442-5453, vol. 9.
Alfonso R. Gennaro, Remington: The Science and Practice of Pharmacy, 20th Edition, (Lippincott, Williams and Wilkins), 2000.
John E. Hoover, Remington's Pharmaceutical Sciences, Mack Publishing Co., Easton Pennsylvania, Fifteenth Edition, 1975.
Liberman et al., Pharmaceutical Dosage Forms: Tablets vols. 1-3, Marcel Decker, New York, N. Y., 1980.
Kibbe et al., Handbook of Pharmaceutical Excipients, Third Edition, American Pharmaceutical Association, Washington, D.C., 1999.
Office Action dated Mar. 28, 2008 from the U.S. Patent and Trademark Office.
Response to the Non-Final Office Action dated Mar. 28, 2008.
Office Action dated Nov. 17, 2008 from the U.S. Patent and Trademark Office.
Response to the Non-Final Office Action dated Nov. 17, 2008.
Advisory Action dated Apr. 1, 2009 from the U.S. Patent and Trademark Office.
Response to the Advisory Office Action dated Apr. 1, 2009 and Final Office Action dated Nov. 17, 2009.

* cited by examiner

*Primary Examiner* — Charanjit Aulakh
(74) *Attorney, Agent, or Firm* — Balaram Gupta; Robert A. Franks; Thomas C. McKenzie (57) ABSTRACT

A 5(S)-(2'-hydroxyethoxy)-20(S)-camptothecin diasterisomer is described which is a better inhibitor of topoisomerase I than either the diastereoisomeric mixture 5(RS)-(2'-hydroxyethoxy)-20(S)-camptothecin, or the 5(R)-(2'-hydroxyethoxy)-20(S)-camptothecin diastereoisomer. Pharmaceutical compositions of the 5(S)-(2'-hydroxyethoxy)-20(S)-camptothecin diastereoisomer are also described as are methods of using the compound for the inhibition of topoisomerase I and for the treatment of cancer.

15 Claims, 2 Drawing Sheets

5(S)-(2'-HYDROXYETHOXY)-20(S)-CAMPTOTHECIN AND ITS PREPARATION AND USE FOR THE TREATMENT OF CANCER

CROSS-REFERENCE TO RELATED PATENTS AND PATENT APPLICATIONS

The subject matter of the present invention is related to U.S. Pat. No. 6,177,439, issued 23 Jan. 2001, and to copending and commonly owned U.S. Pat. No. 7,601,732, issuing 13 Oct. 2009, having the title: Crystalline Form of 5(S)-(2'-hydroxyethoxy)-20(S)-camptothecin, each of which is incorporated herein by reference in its entirety.

The present application is a divisional application of U.S. Non-Provisional application Ser. No. 11/753,432, filed 24 May 2007, which will issue on 13 Oct. 2009, as U.S. Pat. No. 7,601,733, which claims the benefit of India provisional application No. 897/CHE/2006, filed 24 May 2006, and of U.S. Provisional Application No. 60/887,416, filed 31 Jan. 2007, each of which is relied on herein and incorporated herein by reference in its entirety.

BACKGROUND OF THE INVENTION (1) Field of the Invention

The present invention relates to the preparation of the 5(S)-(2'-hydroxyethoxy)-20(S)-camptothecin diastereoisomer of camptothecin and its use for the treatment of cancer.

(2) Description of the Related Art

Camptothecin (CPT) is a pentacyclic plant alkaloid first isolated from the Chinese tree *Camptotheca acuminate* by Wall et al., *J. Am. Chem. Soc.*, 88: 3888 (1966). The structure of camptothecin is shown in formula I:

(I)

Without modification, camptothecin is highly lipophilic and poorly water soluble. Early clinical trials using sodium camptothecin solubilized by sodium hydroxide in water showed that the compound had antineoplastic activity, and further research demonstrated that the activity was due to the action of the compound as an inhibitor of DNA topoisomerase I. However, the therapeutic potential of camptothecin has thus far failed to be fully realized on account of toxicity problems and limited water solubility.

Attempts to provide improved properties for this compound have included the synthesis and testing of numerous analogues of camptothecin. For example, U.S. Pat. No. 5,004,758 describes water soluble camptothecin analogues, U.S. Pat. No. 5,734,056 describes camptothecin analogues. Topotecan, an analogue of camptothecin, is discussed in U.S. Pat. No. 5,004,758, and U.S. Patent Publication US 2007/0105885.

Various Carbon-5 substituted analogues of 20(S)-camptothecin are described in U.S. Pat. No. 6,177,439. One such analogue, 5(RS)-(2'-hydroxyethoxy)-20(S)-camptothecin has the structure shown in formula II:

(II)

The U.S. Pat. No. 6,177,439 discloses processes for the preparation of the diastereoisomeric mixture of this analogue—referred to herein as 5(RS)-(2'-hydroxyethoxy)-20(S)-camptothecin, or as 5-(2'-hydroxyethoxy)-20(S)-camptothecin.

5(RS)-(2'-hydroxyethoxy)-20(S)-camptothecin is a 5-alkoxy substituted 20(S)-camptothecin analog having a pentacyclic structure. It has chiral centers at Carbon-5 and Carbon-20 positions. The Carbon-20 chiral center corresponds to the natural S-configuration. However, the Carbon-5 substitution represents both R and S diastereoisomers in an approximately equal ratio. The molecular formula of 5(RS)-(2'-hydroxyethoxy)-20(S)-camptothecin is $C_{22}H_{20}N_2O_6$. The compound has a molecular weight of 408.41 g/mole and a melting point of 190° C. The diastereoisomeric mixture 5(RS)-(2'-hydroxyethoxy)-20(S)-camptothecin, which can also be referred to as 5-(2'-hydroxyethoxy)-20(S)-camptothecin has poor water solubility.

The 5(S)-(2'-hydroxyethoxy)-20(S)-camptothecin diastereomer of 5(RS)-(2'-hydroxyethoxy)-20(S)-camptothecin is described chemically as 5(S)-(2-hydroxyethoxy)-20(S)-camptothecin, whereas the 5(R)-(2'-hydroxyethoxy)-20(S)-camptothecin diastereomer of 5(RS)-(2'-hydroxyethoxy)-20(S)-camptothecin is described chemically as 5(R)-(2'-hydroxyethoxy)-20(S)-camptothecin. 5(S)-(2'-hydroxyethoxy)-20(S)-camptothecin is also chemically described as 4-(S)-Ethyl-4-hydroxy-12(S)-(2-hydroxyethoxy)-1,12-dihydro-4H-2-oxa-6,12a-diazadibenzo[b,h]fluorene-3,13-dione, which has the following chemical structure shown in formula III:

(III)

5(R)-(2'-hydroxyethoxy)-20(S)-camptothecin has the chemical structure shown in formula IV.

(IV)

Generally speaking, isomers that are enantiomers have, when present in a symmetric environment, identical chemical and physical properties except for their ability to rotate plane-polarized light by equal amounts but in opposite directions. On the other hand, isomers that are diastereomers (or diastereoisomers) are stereoisomers that are not enantiomers. Diastereomers can, and most often do, have different physical properties and different reactivity. In another definition diastereomers are pairs of isomers that have opposite configurations at one or more of the chiral centers but are not mirror images of each other.

Thus, it is clear from the foregoing that it would be desirable to provide the benefits of camptothecin in the treatment of cancer while reducing or avoiding one or more of the undesirable side effects or disadvantages that has heretofore limited its usefulness.

SUMMARY OF THE INVENTION

Briefly, therefore the present invention is directed to a novel 5(S)-(2'-hydroxyethoxy)-20(S)-camptothecin diastereoisomer which is substantially free of 5(R)-(2'-hydroxyethoxy)-20(S)-camptothecin diastereoisomer.

The present invention is also directed to a novel method of inhibiting the activity of topoisomerase I in a cell, the method comprising administering to the cell a topoisomerase I inhibiting effective amount of 5(S)-(2'-hydroxyethoxy)-20(S)-camptothecin which is substantially free of 5(R)-(2'-hydroxyethoxy)-20(S)-camptothecin.

The present invention is also directed to a novel pharmaceutical composition comprising the 5(S)-(2'-hydroxyethoxy)-20(S)-camptothecin as described above and a pharmaceutically acceptable carrier.

The present invention is also directed to a novel method of using 5(S)-(2'-hydroxyethoxy)-20(S)-camptothecin for the production of a pharmaceutical composition, the method comprising intermixing the 5(S)-(2'-hydroxyethoxy)-20(S)-camptothecin described above with a pharmaceutically acceptable carrier.

The present invention is also directed to a novel method of making the 5(S)-(2'-hydroxyethoxy)-20(S)-camptothecin described above, the method comprising the steps:

a) intermixing 5(RS)-(2'-hydroxyethoxy)-20(S)-camptothecin with a solvent selected from n-butanol or tetrahydrofuran;

b) refluxing the mixture for a period of from about 1 to about 4 hours;

c) cooling the mixture to a temperature of from about 40° C. to about 50° C.; and d) separating solid 5(S)-(2'-hydroxyethoxy)-20(S)-camptothecin from the mixture.

The present invention is also directed to a novel method of using 5(S)-(2'-hydroxyethoxy)-20(S)-camptothecin to treat cancer in a subject, the method comprising administering to the subject an effective amount of the 5(S)-(2'-hydroxyethoxy)-20(S)-camptothecin described above.

Among the several advantages found to be achieved by the present invention, therefore, may be noted the provision of a method and composition to provide the benefits of camptothecin in the treatment of cancer while reducing or avoiding one or more of the undesirable side effects or disadvantages that has heretofore limited its usefulness.

DETAILED DESCRIPTION OF THE PREFERRED EMBODIMENTS

Figure 1:
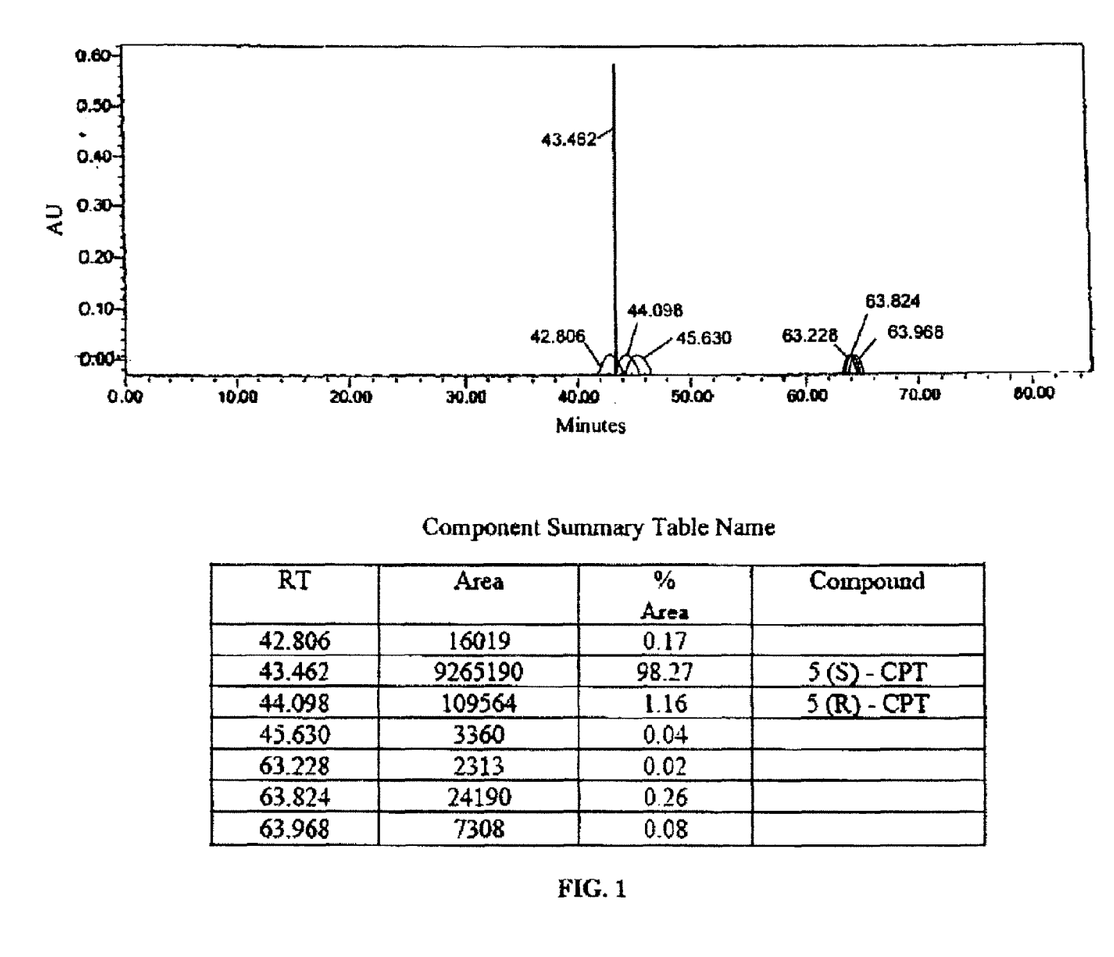
FIG. 1 shows an HPLC chromatogram of one sample of 5(S)-(2'-hydroxyethoxy)-20(S)-camptothecin.
Figure 2:
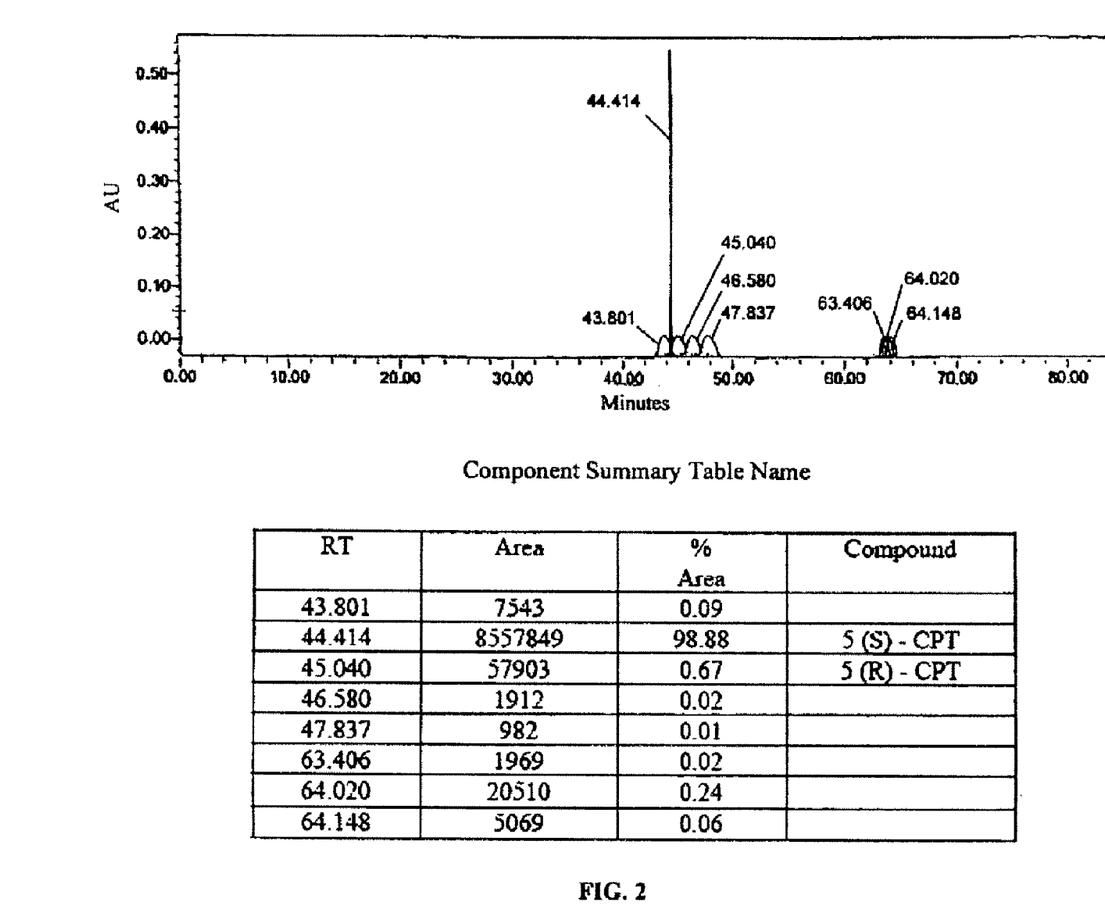
FIG. 2 shows an HPLC chromatogram of another sample of 5(S)-(2'-hydroxyethoxy)-20(S)-camptothecin.

In accordance with the present invention, it has been discovered that the 5(S)-(2'-hydroxyethoxy)-20(S)-camptothecin diastereoisomer is a significantly better inhibitor of topoisomerase I than either the diastereoisomeric mixture 5(RS)-(2'-hydroxyethoxy)-20(S)-camptothecin or the 5(R)-(2'-hydroxyethoxy)-20(S)-camptothecin diastereoisomer. In fact, 5(S)-(2'-hydroxyethoxy)-20(S)-camptothecin is over 20-fold more potent than 5(R)-(2'-hydroxyethoxy)-20(S)-camptothecin and almost 12-fold more potent than the diastereoisomeric mixture 5(RS)-(2'-hydroxyethoxy)-20(S)-camptothecin.

Furthermore, the 5(S)-(2'-hydroxyethoxy)-20(S)-camptothecin diastereoisomer has been shown to be a better inhibitor of the growth of tumors and of cancerous cells than either the diastereoisomeric mixture 5(RS)-(2'-hydroxyethoxy)-20(S)-camptothecin, or the 5(R)-(2'-hydroxyethoxy)-20(S)-camptothecin diastereoisomer.

Unexpectedly, however, the increased anti-cancer activity of the 5(S)-(2'-hydroxyethoxy)-20(S)-camptothecin diastereoisomer is not accompanied by a commensurate increase in toxicity to normal human cells. In fact, when the in vitro potency of the 5(S)-(2'-hydroxyethoxy)-20(S)-camptothecin5(S)-(2'-hydroxyethoxy)-20(S)-camptothecin diastereoisomer against cancer cell lines is compared with its in vitro toxicity in healthy human cells, it is found that the safety margin ($GI_{90}/GI_{50}$) is over twice that of the 5(R)-(2'-hydroxyethoxy)-20(S)-camptothecin diastereoisomer.

Moreover, the presence of the 5(R)-(2'-hydroxyethoxy)-20(S)-camptothecin diastereoisomer has a negative effect on the bioavailability of the 5(S)-(2'-hydroxyethoxy)-20(S)-camptothecin diastereoisomer. Consequently, it is advantageous to administer the 5(S)-(2'-hydroxyethoxy)-20(S)-camptothecin diastereoisomer that is substantially free of the 5(R)-(2'-hydroxyethoxy)-20(S)-camptothecin diastereoisomer to a subject for the treatment of cancer.

To describe the present invention, certain terms are defined herein as follows.

The terms "5(S)-(2'-hydroxyethoxy)-20(S)-camptothecin" is intended to cover not only the more active lactone form of 5(S)-(2'-hydroxyethoxy)-20(S)-camptothecin, but also the less active carboxylate form, including any salts formed therefrom.

The term "inhibit" and variations thereof refer to any reduction of a cellular activity, such as topoisomerase I activity, which can be measured via methods described herein.

The terms "pharmaceutically acceptable", which are further defined below, refer to those active agents, hydrates, solvates, salts, polymorphs, carriers, and the like, which are, within the scope of sound medical judgment, suitable for use in contact with the tissues of humans and lower animals without undue toxicity, irritation, allergic response and the like, commensurate with a reasonable benefit/risk ratio, and effective for their intended use.

The term "individual", "subject" and "patient", as used herein, and which are further defined in more detail below, refer to any animal for whom diagnosis, treatment, or therapy is desired. The term "animals" as used herein refers to humans and other mammals, as well as other animals.

The terms "treating" and "treatment" of a state, disorder, disease or condition as used herein refer to (1) preventing or delaying the appearance of clinical symptoms of the state, disorder, disease or condition developing in a patient that may be afflicted with or predisposed to the state, disorder, disease or condition but does not yet experience or display clinical or subclinical symptoms of the state, disorder or condition, (2) inhibiting the state, disorder, disease or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a patient to be treated is either statistically significant or at least perceptible to the patient and/or to the physician.

The terms "effective amount" and "therapeutically effective amount", as used herein, and which are further defined in more detail below, refer to the amount of a compound that, when administered to a patient for treating a state, disorder, disease or condition, is sufficient to effect such treatment. The effective amount or therapeutically effective amount will vary depending on the compound, the disease and its severity, and the age, weight, physical condition and responsiveness of the individual to be treated.

The terms "delivering" and "administering", as used herein, and which are further defined in more detail below, refer to providing a therapeutically effective amount of an active agent to a particular location or locations within a patient causing a therapeutically effective concentration of the active ingredient at the particular location or locations. This can be accomplished, e.g., by local or by systemic administration of the active ingredient to the host, as will be discussed in more detail below.

The term "composition", as used herein, refers to a product comprising the specified agent or agents, as well as any product, which results, directly or indirectly, from combination of the specified ingredients. A "pharmaceutical composition", which is described in more detail below, is intended to include the combination of an active agent or agents with one or more pharmaceutically acceptable carriers, inert or active, making the composition suitable for diagnostic or therapeutic use in vivo, in vitro or ex vivo. The compositions can also include stabilizers, preservatives, adjuvants, fillers, flavors and other excipients.

As used herein in reference to camptothecin, the terms "Carbon-5 position" refer to the carbon atom present at the $5^{th}$ position of the chemical structure of 5(S)-(2-hydroxyethoxy)-20(S)-camptothecin as shown in formula II above, and the terms "Carbon-20 position" refer to the carbon atom present at the $20^{th}$ position of the chemical structure of 5(S)-(2-hydroxyethoxy)-20(S)-camptothecin as shown in formula II.

As used herein, throughout the present description "5(S)-(2'-hydroxyethoxy)-20(S)-camptothecin" refers to "5(S)-(2'-hydroxyethoxy)-20(S)-camptothecin", which is chemically known as "4(S)-Ethyl-4-hydroxy-12(S)-(2-hydroxyethoxy)-1,12-dihydro-4H-2-oxa-6,12a-diaza-dibenzo[b,h]fluorine-3,13-dione".

As used herein, throughout the present description "5(R)-(2'-hydroxyethoxy)-20(S)-camptothecin" refers to "5(R)-(2'-hydroxyethoxy)-20(S)-camptothecin", which is chemically known as "4(S)-Ethyl-4-hydroxy-12(R)-(2-hydroxyethoxy)-1,12-dihydro-4H-2-oxa-6,12a-diaza-dibenzo[b,h]fluorine-3,13-dione".

As used herein, throughout the present description "5(RS)-(2'-hydroxyethoxy)-20(S)-camptothecin" refers to "5(RS)-(2'-hydroxyethoxy)-20(S)-camptothecin" or "5-(2'-hydroxyethoxy)-20(S)-camptothecin", which is chemically known as "4(S)-Ethyl-4-hydroxy-12(RS)-(2-hydroxyethoxy)-1,12-dihydro-4H-2-oxa-6,12a-diaza-dibenzo[b,h]fluorine-3,13-dione".

As used herein, the term "about", when referring to a measured quantity, refers to the normal variation in that measured quantity as would be expected by the skilled person making the measurement and exercising a level of care commensurate with the objective of measurement and the precision of the measuring equipment.

The terms "substantially free from" are defined below.

Example 26 of the '439 patent described the preparation of 5-(2'-hydroxyethoxy)-20(S)-camptothecin, which is a mixture of R- and S-diastereomers, namely, 5(R)-(2'-hydroxyethoxy)-20(S)-camptothecin and 5(S)-(2'-hydroxyethoxy)-20(S)-camptothecin, respectively. It has now been discovered that 5(S)-(2'-hydroxyethoxy)-20(S)-camptothecin has certain unexpectedly improved properties in comparison to 5(R)-(2'-hydroxyethoxy)-20(S)-camptothecin and 5(RS)-(2'-hydroxyethoxy)-20(S)-camptothecin. As discussed briefly above, the inventors have found that 5(S)-(2'-hydroxyethoxy)-20(S)-camptothecin differs from the diastereomeric mixture 5(RS)-(2'-hydroxyethoxy)-20(S)-camptothecin in several important characteristics, including, for example, toxicity, in vivo anti-tumor activity, bioavailability and topoisomerase I inhibition. Furthermore, it has now been also discovered that 5(S)-(2'-hydroxyethoxy)-20(S)-camptothecin substantially free from 5(R)-(2'-hydroxyethoxy)-20(S)-camptothecin is a desirable anti-cancer pharmaceutical compound.

One aspect of the present invention is 5(S)-(2'-hydroxyethoxy)-20(S)-camptothecin which is substantially free of 5(R)-(2'-hydroxyethoxy)-20(S)-camptothecin.

When it is said that the 5(S)-(2'-hydroxyethoxy)-20(S)-camptothecin is substantially free of 5(R)-(2'-hydroxyethoxy)-20(S)-camptothecin it is meant that the amount of 5(R)-(2'-hydroxyethoxy)-20(S)-camptothecin that is present in a compound comprising both 5(S)-(2'-hydroxyethoxy)-20(S)-camptothecin and 5(R)-(2'-hydroxyethoxy)-20(S)-camptothecin is less than about 2% by weight of the total amount of 5(S)-(2'-hydroxyethoxy)-20(S)-camptothecin and 5(R)-(2'-hydroxyethoxy)-20(S)-camptothecin that is present. The amount of 5(R)-(2'-hydroxyethoxy)-20(S)-camptothecin can be less than about 1.5% w/w, or it can be less than about 1%, and it can be less than about 0.5%, or even less than 0.1% w/w.

In a variant of this aspect, the present compound is substantially optically pure. In an embodiment of this aspect, the compound has overall chemical purity of over 98%.

In another embodiment of the present invention, there is provided 5(S)-(2'-hydroxyethoxy)-20(S)-camptothecin containing less than about 1.5% of the camptothecin heterodimer shown in formula V, or it can contain less than about 1% of the heterodimer of formula V, or less than about 0.8% of the heterodimer, or even less than about 0.5% of the heterodimer, and even less than about 0.1% of the heterodimer, all on a w/w basis.

(V)

In another aspect, there is provided a process for preparing 5(S)-(2'-hydroxyethoxy)-20(S)-camptothecin that is substantially free of 5(R)-(2'-hydroxyethoxy)-20(S)-camptothecin. The method comprises the steps of:

a) providing a solution and/or suspension of 5(RS)-(2'-hydroxyethoxy)-20(S)-camptothecin in an organic solvent in which said 5(S)-(2'-hydroxyethoxy)-20(S)-camptothecin has lower solubility than said 5(R)-(2'-hydroxyethoxy)-20(S)-camptothecin (n-butanol or tetrahydrofuran can be used);

b) heating the solution and/or suspension;

c) cooling the solution and/or suspension so that a precipitate is formed; and d) isolating the precipitate to yield said 5(S)-(2'-hydroxyethoxy)-20(S)-camptothecin substantially free from 5(R)-(2'-hydroxyethoxy)-20(S)-camptothecin.

The process may include the heating step that comprises refluxing the solution and/or suspension. The process may further comprise refluxing the isolated precipitate with additional portions of the organic solvent.

In particular, the method of making the 5(S)-(2'-hydroxyethoxy)-20(S)-camptothecin can comprise the steps:

a) intermixing 5(RS)-(2'-hydroxyethoxy)-20(S)-camptothecin with a solvent selected from n-butanol or tetrahydrofuran;

b) refluxing the mixture for a period of from about 1 to about 4 hours;

c) cooling the mixture to a temperature of from about 40° C. to about 50° C.;

d) separating solid 5(S)-(2'-hydroxyethoxy)-20(S)-camptothecin from the mixture.

If a purer 5(S)-(2'-hydroxyethoxy)-20(S)-camptothecin product is desired, the method can further comprise the steps:

e) washing the solid 5(S)-(2'-hydroxyethoxy)-20(S)-camptothecin with a solvent selected from n-butanol or tetrahydrofuran; and d) drying the solid 5(S)-(2'-hydroxyethoxy)-20(S)-camptothecin to yield 5(S)-(2'-hydroxyethoxy)-20(S)-camptothecin that is substantially free of 5(R)-(2'-hydroxyethoxy)-20(S)-camptothecin.

In another aspect, the invention embraces a method for inhibiting topoisomerase I activity in a cell comprising administering to the cell an amount of 5(S)-(2'-hydroxyethoxy)-20(S)-camptothecin which is substantially free from 5(R)-(2'-hydroxyethoxy)-20(S)-camptothecin, wherein the amount is sufficient to inhibit topoisomerase I (a "topoisomerase I inhibiting effective amount"). The target cell may be cancerous and the administration may be carried out in vitro or in vivo.

The inventors have found that 5(S)-(2'-hydroxyethoxy)-20(S)-camptothecin differs from the diastereomeric mixture 5(RS)-(2'-hydroxyethoxy)-20(S)-camptothecin in several important characteristics, including, for example, toxicity, in vivo anti-tumor activity, bioavailability and topoisomerase I inhibition. Furthermore, it has now been also discovered that 5(S)-(2'-hydroxyethoxy)-20(S)-camptothecin which is substantially free from 5(R)-(2'-hydroxyethoxy)-20(S)-camptothecin is a desirable anti-cancer pharmaceutical compound.

In the present invention, 5(S)-(2'-hydroxyethoxy)-20(S)-camptothecin is administered to a subject according to standard routes of drug delivery that are well known to one of ordinary skill in the art for the purpose of treating cancer.

The 5(S)-(2'-hydroxyethoxy)-20(S)-camptothecin can be supplied as a pure compound, or in the form of a pharmaceutically active salt. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

Suitable pharmaceutically-acceptable base addition salts of compounds of the present invention include metallic ion salts and organic ion salts. More preferred metallic ion salts include, but are not limited to appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

The present 5(S)-(2'-hydroxyethoxy)-20(S)-camptothecin can be provided in a pharmaceutically acceptable carrier and excipient (wherein all "carriers" and "excipients" can be described by either term) to form a pharmaceutical composition. Pharmaceutically acceptable carriers and excipients include, but are not limited to, physiological saline, Ringer's solution, phosphate solution or buffer, buffered saline and other carriers known in the art. Pharmaceutical compositions may also include stabilizers, anti-oxidants, colorants, and diluents. Pharmaceutically acceptable carriers and additives are chosen such that side effects from the pharmaceutical compound are minimized and the performance of the compound is not canceled or inhibited to such an extent that treatment is ineffective.

In an embodiment of the present invention, the pharmaceutical composition containing 5(S)-(2'-hydroxyethoxy)-20(S)-camptothecin is optionally substantially free of 5(R)-(2'-hydroxyethoxy)-20(S)-camptothecin.

The pharmaceutical composition typically contains from 0.1 to 50% w/w, preferably 1 to 20% w/w, of active 5(S)-(2'-hydroxyethoxy)-20(S)-camptothecin compound, the remainder of the composition being the pharmaceutically acceptable carrier or carriers, diluents or solvents. Preferably, the pharmaceutical composition is in a unit dosage form containing appropriate quantities of the active compound, e.g., an amount effective to achieve the desired purpose.

The present pharmaceutical compositions may be administered enterally and/or parenterally. Oral (intra-gastric) is a preferred route of administration. Pharmaceutically acceptable carriers can be in solid dosage forms for the methods of the present invention, which include tablets, capsules, pills, and granules, which can be prepared with coatings and shells, such as enteric coatings and others well known in the art. Liquid dosage forms for oral administration include pharmaceutically acceptable emulsions, solutions, suspensions, syrups, and elixirs.

Parenteral administration includes subcutaneous, intramuscular, intradermal, intramammary, intravenous, and other administrative methods known in the art. Enteral administration includes solution, tablets, sustained release capsules, enteric coated capsules, and syrups. When administered, the pharmaceutical composition may be at or near body temperature.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the 5(S)-(2'-hydroxyethoxy)-20(S)-camptothecin is mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, or olive oil.

Aqueous suspensions can be produced that contain the 5(S)-(2'-hydroxyethoxy)-20(S)-camptothecin in a mixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the 5(S)-(2'-hydroxyethoxy)-20(S)-camptothecin in an omega-3 fatty acid, a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol.

Dispersible powders and granules suitable for preparation of an aqueous suspension by the addition of water provide the 5(S)-(2'-hydroxyethoxy)-20(S)-camptothecin in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

The 5(S)-(2'-hydroxyethoxy)-20(S)-camptothecin and compositions comprising the same can also be administered parenterally, either subcutaneously, or intravenously, or intramuscularly, or intrasternally, or by infusion techniques, in the form of sterile injectable aqueous or olagenous suspensions. Such suspensions may be formulated according to the known art using those suitable dispersing of wetting agents and suspending agents which have been mentioned above or other acceptable agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n-3 polyunsaturated fatty acids may find use in the preparation of injectables.

Administration can also be by inhalation, in the form of aerosols or solutions for nebulizers, or rectally, in the form of suppositories prepared by mixing the drug with a suitable non-irritating excipient which is solid at ordinary temperature, but liquid at the rectal temperature and will therefore, melt in the rectum to release the drug. Such materials are cocoa butter and polyethylene glycols.

Also encompassed by the present invention is buccal or "sub-lingual" administration, which includes lozenges or a chewable gum comprising the compounds, set forth herein. The compounds can be deposited in a flavored base, usually sucrose, and acacia or tragacanth, and pastilles comprising the compounds in an inert base such as gelatin and glycerin or sucrose and acacia.

Topical delivery systems are also encompassed by the present invention and include ointments, powders, sprays, creams, jellies, collyriums, solutions or suspensions.

Powders have the advantage of sticking to moist surfaces, and consequently, can remain active for longer periods. Therefore, powders are especially attractive for treating cancers in, for example the otic canal. For much the same reason, creams are also effective pharmaceutically acceptable carriers.

The compositions of the present invention can optionally be supplemented with additional agents such as, for example, viscosity enhancers, preservatives, surfactants and penetration enhancers.

Such viscosity-building agents include, for example, polyvinyl alcohol, polyvinyl pyrrolidone, methylcellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

Preservatives are optionally employed to prevent microbial contamination during use. Suitable preservatives include: polyquarternium-1, benzalkonium chloride, thimerosal, chlorobutanol, methyl paraben, propyl paraben, phenylethyl alcohol, edetate disodium, sorbic acid, or other agents known to those skilled in the art. The use of polyquarternium-1 as the antimicrobial preservative is preferred. Typically, such preservatives are employed at a level of from 0.001% to 1.0% by weight.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g. Pluronic F-68, F-84 and P-103), cyclodextrin, or other agents known to those skilled in the art. Typically, such co-solvents are employed at a level of from 0.01% to 2% by weight.

Pharmaceutically acceptable excipients and carriers encompass all the foregoing and the like. The above considerations concerning effective formulations and administration procedures are well known in the art and are described in standard textbooks. See e.g. Gennaro, A. R., Remington: The Science and Practice of Pharmacy, 20th Edition, (Lippincott, Williams and Wilkins), 2000; Hoover, John E., Remington's Pharmaceutical Sciences, Mack Publishing Co., Easton Pa., 1975; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

For purposes of the present invention, it is preferred that the amount of 5(S)-(2'-hydroxyethoxy)-20(S)-camptothecin comprises an effective amount of the compound. Thus, the present invention encompasses a method of preventing or treating cancer, neoplasia, and/or a neoplasia-related disease or disorder (which together will be referred to herein as "cancer"), where such treatment preferably is administered to a subject in need of such prevention or treatment, the method comprising administering an effective amount of the 5(S)-(2'-hydroxyethoxy)-20(S)-camptothecin as described herein to a subject.

In determining the effective amount or dose of 5(S)-(2'-hydroxyethoxy)-20(S)-camptothecin, a number of factors are considered by the attending diagnostician, including, but not limited to, the potency and duration of action of the compounds used, the nature and severity of the illness to be treated, as well as the sex, age, weight, general health and individual responsiveness of the patient to be treated, and other relevant circumstances. It will be appreciated that the amount of the 5(S)-(2'-hydroxyethoxy)-20(S)-camptothecin required for use in the treatment or prevention of cancer will vary within wide limits and will be adjusted to the individual requirements in each particular case.

For any compound, the therapeutically effective dose can be estimated initially either in cell culture or in animal models. The therapeutically effective dose refers to the amount of active compound that ameliorates the condition or its symptoms. Therapeutic efficacy and toxicity in cell cultures or animal models may be determined by standard pharmaceutical procedures (e.g., $ED_{50}$: the dose therapeutically effective in 50% of the population; $LD_{50}$: the dose lethal to 50% of the population). The data obtained from cell culture and animal models can then be used to formulate a range of dosage for the compound for use in patients.

In general, for administration to adults, an appropriate daily dosage is described herein, although the limits that are identified as being preferred may be exceeded if expedient. The daily dosage can be administered as a single dosage or in divided dosages. Those skilled in the art will appreciate that dosages may also be determined with guidance from Goodman & Goldman's *The Pharmacological Basis of Therapeutics*, Ninth Edition (1996), Appendix II, pp. 1707-1711. A typical recommended daily dosage regimen will generally range from about 0.01 mg/kg/day to about 50 mg/kg/day, or from about 0.05 mg/kg/day to about 25 mg/kg/day, or from about 0.1 mg/kg/day to about 10 mg/kg/day, or from about 0.1 mg/kg/day to about 5 mg/kg/day, or even from about 0.2 mg/kg/day to about 3 mg/kg/day.

In one embodiment, the crystalline 5(S)-CPT can be provided as hard gelatin capsules for oral administration containing from about 1 mg to about 1000 mg of 5(S)-CPT per capsule, or from about 2 mg to about 500 mg, or from about 5 mg to about 250 mg of 5(S)-CPT per capsule. When the subject to which the 5(S)-CPT is administered is an adult human, the daily dosage of the 5(S)-CPT can be from about 0.01 mg/kg/day to about 50 mg/kg/day, or from about 0.05 mg/kg/day to about 25 mg/kg/day, or from about 0.1 mg/kg/day to about 10 mg/kg/day, or from about 0.1 mg/kg/day to about 5 mg/kg/day, or even from about 0.2 mg/kg/day to about 3 mg/kg/day.

As used herein, the term "subject" for purposes of treatment includes any subject, and preferably is a subject who is in need of the treatment of cancer. As used herein, the terms "subject in need of" refer to any subject who is suffering from or is predisposed to cancer. The terms "subject in need of" also refer to any subject that requires a lower dose of conventional cancer treatment agents. In addition, the terms "subject in need of" means any subject who requires a reduction in the side-effects of a conventional treatment agent. Furthermore, the terms "subject in need of" means any subject who requires improved tolerability to any conventional treatment agent for cancer therapy.

The subject is typically an animal, and yet more typically is a mammal. "Mammal", as that term is used herein, refers to any animal classified as a mammal, including humans, domestic and farm animals, zoo, sports, or pet animals, such as dogs, horses, cats, cattle, etc. The subject may also be a human subject who is at risk for developing cancer or at risk for a relapse of cancer.

The methods and compositions of the present invention may be used for the treatment or prevention of several cancers including, but not limited to, ovarian cancer, osteosarcoma, leukemia, lymphoma, small cell lung cancer, non-small cell lung cancer, central nervous system (CNS) cancer, breast cancer, colorectal cancer, renal cancer, bladder cancer, breast cancer, epidermoid cancer, lung cancer, melanoma, prostate cancer, uterine cancer, soft tissue sarcoma, pancreatic cancer and rhabdomyosarcoma.

The compounds and preparations of the present invention can also be used for the treatment of colon cancer, ovarian cancer and osteosarcoma.

The compounds and preparations of the present invention can also be used for the treatment of osteosarcoma, colorectal cancer and pancreatic cancer.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

Example 1

This example shows the improved topoisomerase I inhibition activity of 5(S)-(2'-hydroxyethoxy)-20(S)-camptothecin as compared against the 5(RS)-(2'-hydroxyethoxy)-20(S)-camptothecin diastereoisomeric mixture and against the 5(R)-(2'-hydroxyethoxy)-20(S)-camptothecin diastereoisomer.

Preparation of 5(S)-(2'-hydroxyethoxy)-20(S)-camptothecin, 5(R)-(2'-hydroxyethoxy)-20(S)-camptothecin and 5(RS)-(2'-hydroxyethoxy)-20(S)-camptothecin A diastereoisomeric mixture of 5(RS)-(2'-hydroxyethoxy)-20(S)-camptothecin (75 grams) prepared as described in Example-26 of U.S. Pat. No. 6,177,439, was suspended in n-butanol (about 600 ml) and refluxed over a period of about 2-3 hours. The reaction mass temperature was reduced over a period of about 1 hour to about 40-50° C., and the solid material obtained was filtered, washed with n-butanol (about 15-20 ml) and dried under vacuum at about 50-55° C. to yield solid 5(S)-(2'-hydroxyethoxy)-20(S)-camptothecin substantially free of 5(R)-(2'-hydroxyethoxy)-20(S)-camptothecin. The product was further enriched to yield 5(S)-(2'-hydroxyethoxy)-20(S)-camptothecin that was substantially free of 5(R)-(2'-hydroxyethoxy)-20(S)-camptothecin by repeatedly refluxing in n-butanol (generally 2-4 times; yield 25-35 grams).

5(R)-(2'-hydroxyethoxy)-20(S)-camptothecin was isolated from the mother liquor by dropwise addition of n-heptane followed by filtration using a 10µ Nutche filter.

5(RS)-(2'-hydroxyethoxy)-20(S)-camptothecin (diastereoisomeric mixture) was obtained as described in Example 26 of U.S. Pat. No. 6,177,439.

Topoisomerase I Assay:

Topoisomerase I introduces transient nicks in DNA at specific sites. Detection of these transient DNA nicks requires trapping the enzyme on DNA in a nicked intermediate complex using protein denaturants. The resulting covalent DNA/topo I complexes contain nicked open circular DNA which can be detected by agarose gel electrophoresis (with ethidium bromide). Trapping nicked intermediates is relatively inefficient, however, inhibitors, such as the natural product camptothecin, stabilize the intermediate and lead to an increase in the nicked DNA product. This forms the basis for a mechanistic drug screen designed to allow detection of agents that affect topoisomerase I by stabilizing the cleaved intermediate complex.

The TopoGEN® Topo I Drug Screening Kit (Topogen, Inc., Port Orange, Fla.) is designed to allow the investigator to quickly identify novel inhibitors of topoisomerase I. The kit allows the detection of novel compounds that either stabilize the nicked intermediate or otherwise inhibit catalytic activity of topoisomerase I.

Assay KIT used: Topogen® Drug screening kit,
Manufacturer: TOPOGEN, Cat No: 1018.
Each reaction mix contains:

| | |
|---|---|
| a. 10x Reaction buffer | 2 µl |
| b. TOPO I enzyme | 2 µl |
| c. pHOT I DNA | 1.2 µl (0.5 ug) |
| d. Water | 14.8 µl |
| e. Drug in DMSO | 1 µl |
| Total | 20 µl |

Protocol

The above reaction mixture is incubated at 37° C. for 30 minutes. The reaction is terminated by adding 2 µl of 10% SDS and the mixture is vortexed rapidly (SDS should be added while at 37° C. as cooling the tubes might reseal the nicked DNA). 10× Dye, about 2.5 µl per tube, is added and equal volumes of a mixture of chloroform and isoamyl alcohol (24:1) is added and centrifuged at 13000 rpm for 10 minutes. Samples are loaded on a 1% agarose gel and electrophoresed for 1 hour at 80 volts. The gel was viewed on UV transilluminator and the densitometric estimation of the bands was calculated.

Calculations:

The density of the DNA bands of both super coiled and relaxed forms of DNA was measured using the densitometer. The band intensity of treated (with single concentration of the test drug) and without the drug (i.e., the Control) were recorded. The percentage of relaxed form DNA compared to the supercoiled DNA was calculated for all the lanes including treated and control.

% inhibition of Topoisomerase activity was calculated as:

=(100−(100×(1/% inhibition in Control)×% inhibition in treated))

Table I shows the results of these tests and shows the in vitro topoisomerase I activities of 5(S)-(2'-hydroxyethoxy)-20(S)-camptothecin and 5(R)-(2'-hydroxyethoxy)-20(S)-camptothecin, which were substantially free of each other, compared with the activity of the racemic mixture 5(RS)-(2'-hydroxyethoxy)-20(S)-camptothecin.

TABLE 1

Topoisomerase I activity of 5(S)-(2'-hydroxyethoxy)-20(S)-camptothecin, 5(R)-(2'-hydroxyethoxy)-20(S)-camptothecin and 5(RS)-(2'-hydroxyethoxy)-20(S)-camptothecin.

| COMPOUND | IC$_{50}$ (µM) |
|---|---|
| 5(S)-(2'-hydroxyethoxy)-20(S)-camptothecin | 1.06 |
| 5(R)-(2'-hydroxyethoxy)-20(S)-camptothecin | 22 |
| 5(RS)-(2'-hydroxyethoxy)-20(S)-camptothecin | 12.5 |

The results show that the 5(S)-(2'-hydroxyethoxy)-20(S)-camptothecin is about 21-fold more active than 5(R)-(2'-hydroxyethoxy)-20(S)-camptothecin and about 12 times more active than 5(RS)-(2'-hydroxyethoxy)-20(S)-camptothecin in inhibiting topoisomerase I. Such differences in activity would not be expected based on structural differences between the diastereomers since it is known that, particularly in view of the importance of the E-ring in enzyme activity.

Example 2

This example shows the anti-tumor activity of 5(S)-(2'-hydroxyethoxy)-20(S)-camptothecin against NCI-H460 (human small cell lung carcinoma) xenografts in nude mice versus the activity of 5(RS)-(2'-hydroxyethoxy)-20(S)-camptothecin.

Samples of 5(S)-(2'-hydroxyethoxy)-20(S)-camptothecin and 5(RS)-(2'-hydroxyethoxy)-20(S)-camptothecin were provided as described in Example 1.

Protocol of Comparison Study of 5(RS)-(2'-hydroxyethoxy)-20(S)-camptothecin and 5(S)-(2'-hydroxyethoxy)-20(S)-camptothecin Against NCI-H460 Xenograft in Nude Mice To perform the NCI-H460 xenograft study, NCI-H460 tumor pieces measuring ~60 mm³ were implanted in the space of dorsal lateral flanks of female athymic nude mice to initiate tumor growth. When the tumors were grown to ~150-1000 mm³, animals were randomized into groups of five prior to initiating therapy. Each gram of 5(RS)-(2'-hydroxyethoxy)-20(S)-camptothecin was formulated to contain 102.65 mg active compound, 801.62 mg hydroxylpropyl beta cyclodextran, 80.62 mg dextrose anhydrous and 13.33 mg sodium carbonate. Each gram of 5(S)-(2'-hydroxyethoxy)-20(S)-camptothecin was formulated to contain 105.57 mg active compound, 800.99 mg hydroxylpropyl beta cyclodextran, 80.13 mg dextrose anhydrous and 13.34 mg sodium carbonate. Each gram of placebo was formulated to contain 895.2 mg hydroxylpropyl beta cyclodextran, 89.52 mg dextrose anhydrous and 14.9 mg sodium carbonate. Each formulation was dissolved in 2 ml sterile water and administered through oral route in a (d×5)2 schedule. Tumor diameters were measured twice a week using a vernier caliper.

Tumor volumes were calculated assuming tumors to be ellipsoid using the formula:

$$V=(D \times d^2)/2,$$

where V (mm³) is tumor volume, D is longest diameter in mm and d is shortest diameter in mm. Change in tumor volumes (Δ) for each treated (T) and control (C) group were calculated by subtracting the mean tumor volume on the first day of treatment (starting day) from the mean tumor volume on the specified observation day. These values were used to calculate a percentage growth (% T/C) using the formulas:

$$\% \ T/C=(\Delta T/\Delta C) \times 100, \text{ where } \Delta T>0, \text{ or}$$

$$\% \ T/C=(\Delta T/\Delta Ti) \times 100, \text{ where } \Delta T<0 \text{ and}$$

Ti is the mean tumor volume.

Percentage tumor growth inhibition (% TGI) was then calculated using the formula:

$$\% \ TGI=100-\% \ TC.$$

All of the mice bearing subcutaneous tumors measuring approximately 150-800 mm³ were treated with test compound through oral gavage using a (d×5)2 schedule. Tumor diameters were measured twice in a week using vernier calipers and tumor volumes were calculated assuming tumors to be ellipsoid using the formula V=(D×d²)/2 where V (mm³) is tumor volume, D is longest diameter in mm., and d is shortest diameter in mm. Changes in tumor Volumes (Δ volumes) for each treated (T) and control (C) group are calculated, by subtracting the mean tumor volume on the first day of treatment (starting day) from the mean tumor volume of on the specified observation day. These values are used to calculate a percentage growth (% T/C) using the formula:

$$\% \ T/C=(\Delta T/\Delta C) \times 100 \text{ where } \Delta T>0 \text{ or } =(\Delta T/\Delta Ti) \times 100$$
$$\text{where } \Delta T<0, \text{ where } Ti \text{ is the mean tumor volume}$$
$$\text{at the start of treatment.}$$

Percentage tumor growth inhibition was calculated using the formula: Percentage Tumor growth inhibition=100–% T/C.

Tumor regressions are defined as partial if the tumor volume decreases to 50% or less of the tumor volume at the start of the treatment without dropping below to 63 mm³. Complete regression is defined if the tumor volume drops to below measurable limits (<63 mm³)

The percentage body weight change in comparison to starting day body weight of each animal was calculated using the formula:

Percentage Body weight change=[(Body weight on specified observation day–Body weight on starting day)/Body weight on starting day]×100.

The other parameter observed was mortality.

The results of the tests are shown in Table 2, where the tumor growth inhibition and the mortality is shown for each of the two test compounds and for the control.

TABLE 2

Effect of 5(S)-(2'-hydroxyethoxy)-20(S)-camptothecin and 5(RS)-(2'-hydroxyethoxy)-20(S)-camptothecin on tumor growth inhibition and mortality of nude mice having NCI-H460 (human small cell lung carcinoma) xenografts.

| Compound | Dose (mg/kg) | % Tumor Growth Inhibition | Mortality |
| --- | --- | --- | --- |
| 5(S)-(2'-hydroxyethoxy)-20(S)-camptothecin | 2 | 68 | 0/5 |
|  | 4 | 76 | 0/5 |
| 5(RS)-(2'-hydroxyethoxy)-20(S)-camptothecin | 2 | 60 | 0/5 |
|  | 4 | 64 | 0/5 |

The data from this test showed that 5(S)-(2'-hydroxyethoxy)-20(S)-camptothecin demonstrated better in vivo activity against NCI-H460 (human small cell lung carcinoma) xenografts in nude mice than the diastereoisomer 5(RS)-(2'-hydroxyethoxy)-20(S)-camptothecin. As shown in Table 2, the administration of 5(S)-(2'-hydroxyethoxy)-20(S)-camptothecin led to unexpected increase in the inhibition of tumor growth in comparison with the administration of 5(RS)-(2'-hydroxyethoxy)-20(S)-camptothecin at identical doses (68% vs 60% at 2 mg/kg, and 76% vs 64% at 4 mg/kg) without an increase in mortality.

Example 3

This example illustrates the efficacy of 5(S)-(2'-hydroxyethoxy)-20(S)-camptothecin versus 5(R)-(2'-hydroxyethoxy)-20(S)-camptothecin in inhibiting in vitro cell proliferation in a Sulphorhodamine B (SRB) assay.

Samples of 5(S)-(2'-hydroxyethoxy)-20(S)-camptothecin and 5(R)-(2'-hydroxyethoxy)-20(S)-camptothecin were provided as described in Example 1.

Protocol for In Vitro Cell Growth Assay:

Cell proliferation was evaluated by Sulphorhodamine B (SRB) assay where the amount of dye bound to the cells after staining gives a measure of cell growth. Refer to: *JNCI*, vol 83, No. 11, Jun. 5, 1991, which is incorporated herein by reference.

Briefly, cells (34 human cancer cell lines represented by bladder, breast, CNS, colon, epidermoid, lung, ovarian, melanoma, prostate, renal and uterine cancers) were seeded on a 96-well cell culture plates at a concentration of 10,000 cells per well and incubated at 37° C. in a $CO_2$ incubator. Twenty-four hours later, cells were treated with different concentrations of andrographolide dissolved in DMSO to a final concentration of 0.05% in the culture medium and exposed for 48 h. Cells were fixed by adding ice-cold 50% trichloroacetic acid (TCA) and incubating for 1 h at 4° C. The plates were washed with distilled water, air dried and stained with SRB solution (0.4% wt/vol in 1% Acetic acid) for 10 min at room temperature. Unbound SRB was removed by washing thoroughly with 1% acetic acid and the plates were air-dried. The bound SRB stain was solubilized with 10 mM Tris buffer, and the optical densities were read on a spectrophotometric plate reader at a single wavelength of 515 nm. At the time of drug addition separate reference plate for cell growth at time 0 h (the time at which drugs were added) was also terminated as described above. From the optical densities the percentage growths were calculated using the following formulae:

If $T$ is greater than or equal to $T_0$, percentage growth=$100\times[(T-T_0)/(C-T_0)]$ and if $T$ is less than $T_0$, percentage growth=$100\times[(T-T_0)/T_0]$, Where T is optical density of test, C is the optical density of control and $T_0$ is the optical density at time zero.

From the percentage growths a dose response curve was generated and $GI_{50}$ values were interpolated from the growth curves. Table 3 shows the results.

TABLE 3

GI50 values for 5(S)-(2'-hydroxyethoxy)-20(S)-camptothecin versus 5(R)-(2'-hydroxyethoxy)-20(S)-camptothecin.

| Compound | $GI_{50}$ (µM) |
|---|---|
| 5(S)-(2'-hydroxyethoxy)-20(S)-camptothecin | 5.0 |
| 5(R)-(2'-hydroxyethoxy)-20(S)-camptothecin | 14.6 |

The results of this test showed that the 5(S)-(2'-hydroxyethoxy)-20(S)-camptothecin diastereoisomer was almost three times more active than the 5(R)-(2'-hydroxyethoxy)-20 (S)-camptothecin diastereoisomer against cell proliferation in the test.

Example 4

This example illustrates the efficacy of 5(S)-(2'-hydroxyethoxy)-20(S)-camptothecin in several osteosarcoma tumor models.

Samples of 5(S)-(2'-hydroxyethoxy)-20(S)-camptothecin and 5(RS)-(2'-hydroxyethoxy)-20(S)-camptothecin were provided as described in Example 1.

This test was carried out with the use of the methods described in *Cancer, Res.*, Oct. 15, 64:20:7491-9 (2004), and in *Clin. Cancer Res.*, Nov. 15:9(15):5442-53 (2003).

All mice bearing subcutaneous ("sc") tumors measuring approximately 0.2-1 cm in diameter were treated with a test compound by oral gavage using [(d×5)2]3 schedule. Tumor diameters were measured every 7 days using Vernier calipers and tumor volumes were calculated, assuming tumors to be spherical, using the formula $[\pi/6)\times d^3]$, where d is the mean diameter. The tumor response to the test compound was defined as follows: For individual tumors, partial regression ("PR") was defined as a volume regression >50%, but with measurable tumor at all times. Complete regression ("CR") was defined as disappearance of measurable tumor mass at some point within 12 weeks after initiation of therapy. Maintained CR is defined as no tumor re-growth within a 12-week study time frame. This time point was chosen because all studies lasted at least 12 weeks. Mice that died before the end of the 12-week study time, and prior to achieving a response, were considered as failures for tumor response. The results (dose of 28 mg/kg) are presented in Table 4.

TABLE 4

Efficacy of 5(S)-(2'-hydroxyethoxy)-20(S)-camptothecin versus 5(RS)-(2'-hydroxyethoxy)-20(S)-camptothecin in mouse tumor regression models.

| Xenograft | 5(S)-(2'-hydroxyethoxy)-20(S)-camptothecin | 5(RS)-(2'-hydroxyethoxy)-20(S)-camptothecin |
|---|---|---|
| Osteosarcoma-29 | 6+ | 5+ |
| Osteosarcoma-17 | 6+ | 4+ |
| Osteosarcoma-2 | 6+ | 5+ |
| Osteosarcoma-32 | 6+ | 3+ |

6+: Maintained Complete Regression
5+: Complete Regression
4+: Partial Regression
3+: Stable Disease As shown by the date of Table 4, administration of 5(S)-(2'-hydroxyethoxy)-20(S)-camptothecin led to unexpectedly improved results in comparison with the administration of 5(RS)-(2'-hydroxyethoxy)-20(S)-camptothecin, as indicated by complete regression (6+) achieved with 5(S)-(2'-hydroxyethoxy)-20(S)-camptothecin in all four xenograft lines.

The data provided in Examples 3 and 4 illustrates that 5(S)-(2'-hydroxyethoxy)-20(S)-camptothecin has unexpectedly improved activity/potency profile in several test models. Furthermore, while 5(S)-(2'-hydroxyethoxy)-20(S)-camptothecin is substantially more potent than 5(R)-(2'-hydroxyethoxy)-20(S)-camptothecin, the increase in potency is not accompanied by a commensurate increase in toxicity.

Example 5

This example shows the human bone marrow toxicity of 5(S)-(2'-hydroxyethoxy)-20(S)-camptothecin versus 5(R)-(2'-hydroxyethoxy)-20(S)-camptothecin.

Samples of 5(S)-(2'-hydroxyethoxy)-20(S)-camptothecin and 5(R)-(2'-hydroxyethoxy)-20(S)-camptothecin were provided as described in Example 1.

Protocol for Human Bone Marrow Assay:

Methocult™ GF (Cat No: H4534, Poietics, Biowhittakar, USA) medium comprising Methycellulose in Iscove's MDM, Fetal bovine serum, Bovine serum albumin, 2-Mercaptoethanol, L-Glutamine, rhStem cell factor, rhGM-CSF and rhIL-3 was used for the assay. Human bone marrow mononuclear cells (Cat No. 2M-125C, Poietics, Biowhittakar, USA) were mixed with Methocult GF and the cell density was adjusted to $3\times10^5$ cells/ml. From this preparation, 500 µL aliquots were made and 2.5 µL of 20× drug solution or vehicle was added to each aliquot and mixed thoroughly. 100 µL of clonogenic medium was plated into each well and the plates were allowed to gel at 4° C. for 15 minutes. Plates were incubated at 37° C. in a fully humidified atmosphere of 5% $CO_2$ in an incubator for 14 days. CFU-GM colonies were counted under an inverted microscope as aggregates of 50 cells or more. The percentage colony inhibition was calculated using the following formula:

100−[(number of colonies in drug treated wells/Number of colonies in control wells)×100].

The in vitro potency of the two diastereomers against cancer cell lines had been compared with their in vitro toxicity in healthy cells. Table 5 presents the results of the bone marrow toxicity comparison study in human cells.

TABLE 5

$GI_{90}$ values for 5(S)-(2'-hydroxyethoxy)-20(S)-camptothecin and 5(R)-(2'-hydroxyethoxy)-20(S)-camptothecin for human bone marrow cells in vitro.

| Compound | $GI_{90}$ (μM) |
|---|---|
| 5(S)-(2'-hydroxyethoxy)-20(S)-camptothecin | 0.69 |
| 5(R)-(2'-hydroxyethoxy)-20(S)-camptothecin | 0.89 |

With reference to the date shown in Tables 3 and 5, it can be seen that while 5(S)-(2'-hydroxyethoxy)-20(S)-camptothecin is unexpectedly almost 3 times more potent against 34 human cancer cell lines (including bladder, breast, CNS, colon, epidermoid, lung, ovarian, melanoma, prostate, renal and uterine cancer cells) than 5(R)-(2'-hydroxyethoxy)-20(S)-camptothecin, the toxicities of both diastereomers are comparable. In fact, if the safety margin is estimated as the ratio of $GI_{90}$ for human cell toxicity to $GI_{50}$ for anticancer activity, as shown in Table 6, it is apparent that 5(S)-(2'-hydroxyethoxy)-20(S)-camptothecin is unexpectedly superior to 5(R)-(2'-hydroxyethoxy)-20(S)-camptothecin and 5(RS)-(2'-hydroxyethoxy)-20(S)-camptothecin as a pharmaceutical compound for treatment of cancer. Thus, the 5(S)-(2'-hydroxyethoxy)-20(S)-camptothecin compound has increased efficacy with respect to treatment of cancer in comparison with the R-diastereomer and the mixture of diastereomers. In fact, it is unexpectedly important to minimize the amount of the 5(R)-(2'-hydroxyethoxy)-20(S)-camptothecin present in the 5(S)-(2'-hydroxyethoxy)-20(S)-camptothecin to be given to patients.

TABLE 6

Ratio of $GI_{90}$ for human cell toxicity to $GI_{50}$ for anticancer activity for 5(S)-(2'-hydroxyethoxy)-20(S)-camptothecin and 5(R)-(2'-hydroxyethoxy)-20(S)-camptothecin.

| Compound | Safety Margin ($GI_{90}/GI_{50}$) |
|---|---|
| 5(S)-(2'-hydroxyethoxy)-20(S)-camptothecin | 0.14 |
| 5(R)-(2'-hydroxyethoxy)-20(S)-camptothecin | 0.06 |

Example 6

This example shows the effect of the presence of 5(R)-(2'-hydroxyethoxy)-20(S)-camptothecin on the bioavailability of 5(S)-(2'-hydroxyethoxy)-20(S)-camptothecin in rats and mice.

Samples of 5(S)-(2'-hydroxyethoxy)-20(S)-camptothecin ("5(S)-CPT") and 5(RS)-(2'-hydroxyethoxy)-20(S)-camptothecin ("5(RS)-CPT") were provided as described in Example 1.

Bioavailability in Male Wistar Rats:

5(S)-CPT (2.5 mg/kg) and 5(RS)-CPT (5 mg/kg, including 2.5 mg/kg of 5(S)-CPT in the mixture) were been administered to male Wistar Rats to evaluate oral pharmacokinetics.

Male Wistar rats, 6-8 weeks of age and weighing between 205 and 218 g were divided into groups of four rats. The oral pharmacokinetics test was carried out in overnight fasted condition and intravenous pharmacokinetics was carried out in fed condition. The test drugs were administered as a solution by oral gavage or lateral tail vein injection. Sparse blood samples of about 250 microliters were collected from retro-orbital plexus at designated time points into microcentrifuge tubes containing 25 microliters of EDTA. Plasma was separated by centrifuging blood at 12,800 rpm for 2 min and refrigerated until analysis.

Samples were tested for the presence of the test drug as follows. An aliquot of 100 μl plasma (stored at 8° C.) was precipitated with 400 μl of cold methanol for the estimation of total (lactone+carboxylate). Following mixing for 2 min. and centrifugation for 4 min. at 12,800 rpm, clear supernatant was separated into a 300 μl auto-sampler vial and 20 μl of this mixture was injected onto an analytical column for HPLC analysis. Concentrations of the test drug were calculated from the linearity plotted by spiking known concentrations of the test drug in blank rat plasma. The pharmacokinetics of the test drug was calculated using non-compartmental analysis.

The results of the study are presented in Table 7.

TABLE 7

Oral pharmacokinetic parameters of 5(S)-CPT in male Wistar rats.

| Compound | Dose | AUC(o-t) μM * h |
|---|---|---|
| 5(S)-CPT | 5 mg/kg | 5.76 |
| 5(RS)-CPT | 5 mg/kg (2.5 mg/kg 5(S)-CPT + 2.5 mg/kg 5(R)-CPT) | 5.08 |
| Contribution of 5(S)-CPT in 5(RS)-CPT | 2.5 mg/kg | 1.21 |

Bioavailability in Swiss Albino Mice:

5(S)-CPT (2.5 mg/kg) and 5(RS)-CPT (5 mg/kg, including 2.5 mg/kg of 5(S)-CPT in the mixture) were been administered to Swiss Albino mice to evaluate oral pharmacokinetics.

Swiss Albino mice, 3-6 weeks of age and weighing between 28-34 g were used in the study. Twelve mice were used per study. The oral pharmacokinetics test was carried out in overnight fasted condition and intravenous pharmacokinetics was carried out in fed condition. The test drugs were administered as a solution by oral gavage or lateral tail vein injection. Sparse blood samples of about 250 microliters were collected from retro-orbital plexus at designated time points into microcentrifuge tubes containing 25 microliters of EDTA. Plasma was separated by centrifuging blood at 12,800 rpm for 2 min and refrigerated until analysis.

Samples were tested for the presence of the test drug as follows. An aliquot of 100 μl plasma (stored at 8° C.) was precipitated with 400 μl of cold methanol for the estimation of total (lactone+carboxylate). Following mixing for 2 min. and centrifugation for 4 min. at 12,800 rpm, clear supernatant was separated into a 300 μl auto-sampler vial and 20 μl of this mixture was injected onto an analytical column for HPLC analysis. Concentrations of the test drug were calculated from the linearity plotted by spiking known concentrations of the test drug in blank rat plasma. The pharmacokinetics of the test drug was calculated using non-compartmental analysis. The results of the study are presented in Table 8.

TABLE 8

Oral pharmacokinetic parameters of 5(S)-CPT in Swiss Albino mice.

| Compound | Dose | AUC(o-t) $\mu M * h$ |
|---|---|---|
| 5(S)-CPT | 5 mg/kg | 5.18 |
| 5(RS)-CPT | 5 mg/kg (2.5 mg/kg 5(S)-CPT + 2.5 mg/kg 5(R)-CPT) | 5.20 |
| Contribution of 5(S)-CPT in 5(RS)-CPT | 2.5 mg/kg | 1.10 |

With reference to Tables 7 and 8, the "Contribution of 5(S)-(2'-hydroxyethoxy)-20(S)-camptothecin" is the Area Under Curve ("AUC") that can be attributed to the S-diastereomer in the RS diastereomeric mixture. As can be seen from Tables 7 and 8, the presence of 5(R)-(2'-hydroxyethoxy)-20(S)-camptothecin unexpectedly decreases bioavailability of the desired 5(S) diastereomer. Moreover, it is believed that such unexpected decrease in bioavailability for the desired diastereomers would also be observed in human patients. On the basis of the above, the inventors have recognized that minimization of the amount of the R diastereomers impurity in 5(S)-(2'-hydroxyethoxy)-20(S)-camptothecin is desirable.

Example 7

This example illustrates the efficacy of 5(S)-(2'-hydroxyethoxy)-20(S)-camptothecin versus 5(R)-(2'-hydroxyethoxy)-20(S)-camptothecin and 5(RS)-(2'-hydroxyethoxy)-20(S)-camptothecin against BCRP mutant and Breast cancer resistance protein (BCRP) over expressing Saos-2 cells.

Samples of 5(S)-(2'-hydroxyethoxy)-20(S)-camptothecin, 5(R)-(2'-hydroxyethoxy)-20(S)-camptothecin and 5(RS)-(2'-hydroxyethoxy)-20(S)-camptothecin were provided as described in Example 1.

Protocol for Breast Cancer Resistance Protein (BCRP) Assay:

The anticancer effect of 5(S)-(2'-hydroxyethoxy)-20(S)-camptothecin & 5(R)-(2'-hydroxyethoxy)-20(S)-camptothecin were evaluated versus the racemate 5(RS)-(2'-hydroxyethoxy)-20(S)-camptothecin on Saos-2 cells over expressing functional BCRP#4 and non-functional BCRP mut#10. The human osteosarcoma cell line, Saos-2, was obtained from ATCC (American Type Culture Collection, Cat#HTB-85, Manassas, Va.) and were maintained in DMEM containing 10% fetal bovine serum, 1% penicillin/streptomycin, and 2 mM glutamine. Saos-2 cells were transfected with either BCRP#4 to over express functional BCRP or BCRP#10 to over express non-functional BCRP transporter. The cells were plated in 96-well plates at a density of 1000 cells per each well in a 0.1 ml of medium and allowed to attach overnight. The next morning the medium was gently aspirated and serial dilutions of the compounds to be tested were added. The cells were incubated at 37° C. in a 5% $CO_2$ incubator. After 6 days of exposure to the test drugs, 10 μl of Alamar blue was added aseptically to each well and the plates were returned to the incubator for 6 hr. The amount of the fluorescent dye produced was measured on a Cytofluor® 2300 (Millipore, Bedford, Mass.) using an excitation wavelength of 530 nm and emission wavelength of 590 nm. The relative fluorescence units obtained were used to calculate the percentage growth at each concentration in relation to the untreated control values. From the percentage growth values the $IC_{50}$ (inhibitory concentration required to inhibit the cell growth by 50% compared to control cells growth) values were derived. The resulting $IC_{50}$ values are presented in Table 9.

TABLE 9

$IC_{50}$ values for 5(S)-(2'-hydroxyethoxy)-20(S)-camptothecin, 5(R)-(2'-hydroxyethoxy)-20(S)-camptothecin and 5(RS)-(2'-hydroxyethoxy)-20(S)-camptothecin against BCRP mutant and Breast cancer resistance protein (BCRP) over expressing Saos-2 cells.

| | $IC_{50}$ (nM) | |
|---|---|---|
| Drug | BCRP mut #10 | BCRP #4 |
| 5(RS)-(2'-hydroxyethoxy)-20(S)-camptothecin | 387 | 1256 |
| 5(S)-(2'-hydroxyethoxy)-20(S)-camptothecin | 213 | 788 |
| 5(R)-(2'-hydroxyethoxy)-20(S)-camptothecin | 1299 | >2000 |

As shown in Table 9, 5(S)-(2'-hydroxyethoxy)-20(S)-camptothecin is superior to 5(R)-(2'-hydroxyethoxy)-20(S)-camptothecin and 5(RS)-(2'-hydroxyethoxy)-20(S)-camptothecin in terms of its cytotoxic activity on BCRP mutant as well as BCRP over expressing Saos-2 cells. These results indicate that the rank order of cytotoxicity on both BCRP mut#10 and BCRP#4 was 5(S)-(2'-hydroxyethoxy)-20(S)-camptothecin>5(RS)-(2'-hydroxyethoxy)-20(S)-camptothecin>5(R)-(2'-hydroxyethoxy)-20(S)-camptothecin. 5(S)-(2'-hydroxyethoxy)-20(S)-camptothecin was ~6 and >2.5 fold more cytotoxic than 5(R)-(2'-hydroxyethoxy)-20(S)-camptothecin on BCRP mut#10 and BCRP#4 over expressing Saos-2 cells, respectively.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions by those of ordinary skill in the art without departing from the scope of the invention, it is intended that all matter contained in the above description and shown in the accompanying drawings shall be interpreted as illustrative and not in a limiting sense. In addition it should be understood that aspects of the various embodiments may be interchanged both in whole or in part.

What is claimed is:

1. 5(S)-(2'-hydroxyethoxy)-20(S)-camptothecin which is substantially free of 5(R)-(2'-hydroxyethoxy)-20(S)-camptothecin.

2. The 5(S)-(2'-hydroxyethoxy)-20(S)-camptothecin according to claim 1, which is substantially optically pure.

3. The 5(S)-(2'-hydroxyethoxy)-20(S)-camptothecin according to claim 1, which has a chemical purity of over 98%.

4. The 5(S)-(2'-hydroxyethoxy)-20(S)-camptothecin according to claim 1, wherein 5(R)-(2'-hydroxyethoxy)-20(S)-camptothecin is present in an amount of less than about 1.5% w/w.

5. The 5(S)-(2'-hydroxyethoxy)-20(S)-camptothecin according to claim 1, wherein 5(R)-(2'-hydroxyethoxy)-20(S)-camptothecin is present in an amount of less than about 1% w/w.

6. The 5(S)-(2'-hydroxyethoxy)-20(S)-camptothecin according to claim 1, wherein 5(R)-(2'-hydroxyethoxy)-20(S)-camptothecin is present in an amount of less than about 0.5% w/w.

7. The 5(S)-(2'-hydroxyethoxy)-20(S)-camptothecin according to claim 1, wherein 5(R)-(2'-hydroxyethoxy)-20(S)-camptothecin is present in an amount of less than about 0.1% w/w.

8. The 5(S)-(2'-hydroxyethoxy)-20(S)-camptothecin according to claim 1, wherein the camptothecin dimer impurity having the chemical structure of formula V is present in the 5(S)-(2'-hydroxyethoxy)-20(S)-camptothecin in an amount of less than about 1.5% w/w (V)

9. The 5(S)-(2'-hydroxyethoxy)-20(S)-camptothecin according to claim 1, wherein the camptothecin dimer impurity having the chemical structure of formula V is present in the 5(S)-(2'-hydroxyethoxy)-20(S)-camptothecin in an amount of less than about 1% w/w 10. The 5(S)-(2'-hydroxyethoxy)-20(S)-camptothecin according to claim 1, wherein the camptothecin dimer impurity having the chemical structure of formula V is present in the 5(S)-(2'-hydroxyethoxy)-20(S)-camptothecin in an amount of less than about 0.1% w/w (V)

11. A pharmaceutical composition comprising the 5(S)-(2'-hydroxyethoxy)-20(S)-camptothecin as described in claim 1 and a pharmaceutically acceptable carrier.

12. The pharmaceutical composition according to claim 11, in a form wherein a single dose of the composition for an adult human comprises from about 5 mg to about 25 mg of 5(S)-(2'-hydroxyethoxy)-20(S)-camptothecin.

13. A method for the preparation of a pharmaceutical composition, the method comprising intermixing the 5(S)-(2'-hydroxyethoxy)-20(S)-camptothecin described in claim 1 with a pharmaceutically acceptable carrier.

14. A method of making the 5(S)-(2'-hydroxyethoxy)-20(S)-camptothecin described in claim 1, the method comprising the steps:
   a) intermixing 5(RS)-(2'-hydroxyethoxy)-20(S)-camptothecin with a solvent selected from n-butanol or tetrahydrofuran;
   b) refluxing the mixture for a period of from about 1 to about 4 hours;
   c) cooling the mixture to a temperature of from about 40° C. to about 50° C.; and
   d) separating solid 5(S)-(2'-hydroxyethoxy)-20(S)-camptothecin from the mixture.

15. The method according to claim 14, further comprising the steps:
   e) washing the solid 5(S)-(2'-hydroxyethoxy)-20(S)-camptothecin with a solvent selected from n-butanol or tetrahydrofuran; and
   f) drying the solid 5(S)-(2'-hydroxyethoxy)-20(S)-camptothecin to yield 5(S)-(2'-hydroxyethoxy)-20(S)-camptothecin that is substantially free of 5(R)-(2'-hydroxyethoxy)-20(S)-camptothecin.

* * * * *